United States Patent
Biggadike et al.

(10) Patent No.: US 7,045,658 B2
(45) Date of Patent: May 16, 2006

(54) FORMAILIDE DERIVATIVES AS BETA2-ADRENORECEPTOR AGONISTS

(75) Inventors: Keith Biggadike, Stevenage (GB); Rita Field, Stevenage (GB); Stephen Barry Guntrip, Stevenage (GB); Brian Edgar Looker, Stevenage (GB)

(73) Assignee: Glaxo Group Limited, Greenford (GB)

(*) Notice: Subject to any disclaimer, the term of this patent is extended or adjusted under 35 U.S.C. 154(b) by 0 days.

(21) Appl. No.: 10/472,343

(22) PCT Filed: Mar. 20, 2002

(86) PCT No.: PCT/EP02/03122

§ 371 (c)(1),
(2), (4) Date: Mar. 5, 2004

(87) PCT Pub. No.: WO02/076933

PCT Pub. Date: Oct. 3, 2002

(65) Prior Publication Data

US 2004/0157830 A1 Aug. 12, 2004

(30) Foreign Application Priority Data

Mar. 22, 2001 (GB) .......... 0107213
Nov. 9, 2001 (GB) .......... 0126995

(51) Int. Cl.
*C07C 311/29* (2006.01)
*A61K 31/18* (2006.01)

(52) U.S. Cl. .......... 564/86; 514/603
(58) Field of Classification Search .......... 564/86; 514/603

See application file for complete search history.

(56) References Cited

U.S. PATENT DOCUMENTS

| | | | |
|---|---|---|---|
| 3,994,974 A | 11/1976 | Murakami et al. | |
| 4,730,008 A | 3/1988 | Skidmore et al. | |
| 4,853,381 A | 8/1989 | Finch et al. | |
| 4,853,382 A | 8/1989 | Skidmore et al. | |
| 4,908,386 A | 3/1990 | Finch et al. | |
| 4,937,268 A | 6/1990 | Skidmore et al. | |
| 4,963,564 A | 10/1990 | Skidmore et al. | |
| 4,990,505 A | 2/1991 | Skidmore et al. | |
| 4,992,474 A | 2/1991 | Skidmore et al. | |
| 4,997,986 A | 3/1991 | Mitchell et al. | |
| 5,066,678 A | 11/1991 | Finch et al. | |
| 5,099,068 A | 3/1992 | Mitchell et al. | |
| 5,109,023 A | 4/1992 | Mitchell et al. | |
| 5,283,262 A | 2/1994 | Mitchell et al. | |
| 5,552,438 A | 9/1996 | Christensen, IV | |

FOREIGN PATENT DOCUMENTS

| | | |
|---|---|---|
| EP | 69715 | 1/1983 |
| EP | 162576 | 11/1985 |
| EP | 220054 | 4/1987 |
| EP | 220878 | 5/1987 |
| EP | 223410 | 5/1987 |
| EP | 286242 | 10/1988 |
| EP | 303465 | 2/1989 |
| EP | 317206 | 5/1989 |
| GB | 2064336 | 6/1981 |
| GB | 2129691 | 5/1984 |
| GB | 2140800 | 12/1984 |
| GB | 2159151 | 11/1985 |
| GB | 2162842 | 2/1986 |
| GB | 2169265 | 7/1986 |
| GB | 2178965 | 2/1987 |
| GB | 0416951 | 9/1991 |
| GB | 2242134 | 9/1991 |
| WO | WO 95/01170 | 1/1995 |
| WO | WO 99/16766 | 4/1999 |
| WO | WO 99/47505 | 9/1999 |
| WO | WO 01/13953 | 3/2001 |

OTHER PUBLICATIONS

D. Iakovidis, et al., "Synthesis and beta–adrenoceptor agonist properties of (+/–)–1–(3',4'–dihydroxyphenoxy)–3–(3", 4"–dimethooxyphenyl)ethylamino–2–propanol hydrochloride, (+/–)–RO363.HCl, and the (2S)–(–)–isomer", Eurpoean Journal of Medicinal Chemistry, vol. 34, no. 6, Jun. 1999, pp. 539–548.

Fuji et al., "Novel phosphodiesterase 4 inhibitor T–440 reverse and prevents human bronchial contraction induced by allergen," *J Pharmacol Exp Ther* 284 (1):162 (1998).

Landells et al., "Oral administration of the phosphodiesterase (PDE)4 inhibitor, V11294 inhibits ex–vivo agonist–induced–cell activation," *Eur Resp J (Iannu Cong Eur Resp Soc, Geneva)* 12(Suppl. 28) abst P2393 (Sep. 1998).

McHale et al., "Expression of human recombinant cAMP phoshodiesterase isozyme IV reverse growth arrest phenotype in phoshodiesterase–deficient yeat," *Mol Pharmacol* 39:109–113 (119).

Nicholson et al., "Different modulation of tissue function and therapeutic potential of selective inhibitors of cyclic nucleotide phosphdiesterase isoenzymes," *Trends Pharmacol Sci* 12;19–27 (1991).

Torphy et al., "Role of cyclic nucleotide phosphodiesterase isozymes in intact canine trachealis," *Mol. Pharmacol* 39:376–384 (1991).

U.S. Appl. No. 10/467,733, Filed Feb. 9, 2004, Biggadike et al.

Thornber, "Isosterism and molecular modification in drug design," *Chemical Society Reviews:* 8(4)563–580 (1979).

*Primary Examiner*—Shailendra Kumar
(74) *Attorney, Agent, or Firm*—Robert J. Smith

(57) ABSTRACT

The present invention relates to novel compounds of formula (I), to a process for their menufacture, to pharmaceutical compositions containing them, and to their use in therapy, in particular their use in the prophylaxis and treatment of respiratory diseases (I)

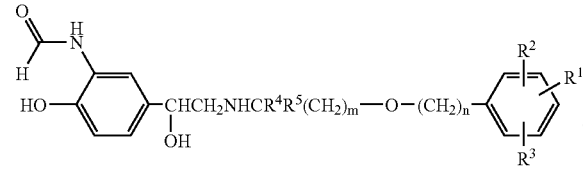

25 Claims, No Drawings

FORMAILIDE DERIVATIVES AS BETA2-ADRENORECEPTOR AGONISTS

CROSS-REFERENCE TO RELATED APPLICATIONS

This application is filed under 35 U.S.C. §371 as the United States National Phase Application of International Application No. PCT/EP02/03122 filed Mar. 20, 2002 claiming priority from Great Britain Application Nos. 0107213.1 and 0126995.0 filed Mar. 22, 2001 and Nov. 9, 2001, the disclosures of which are incorporated herein by reference in their entirety.

The present invention is concerned with phenethanolamine derivatives, processes for their preparation, compositions containing them and their use in medicine, particularly in the prophylaxis and treatment of respiratory diseases.

Certain phenethanolamine compounds are known in the art as having selective stimulant action at $\beta_2$-adrenoreceptors and therefore having utility in the treatment of bronchial asthma and related disorders. Thus GB 2 140 800 describes phenethanolamine compounds including 4-hydroxy-$\alpha^1$-[[[6-(4-phenylbutoxy)hexyl]amino]methyl]-1,3-benzenedimethanol 1-hydroxy-2-naphthalenecarboxylate (salmeterol xinafoate) which is now used clinically in the treatment of such medical conditions.

Formoterol, i.e. 2'-hydroxy-5'-[(RS)-1-hydroxy-2{[(RS)-p-methoxy-$\alpha$-methylphenethyl]amino}ethyl]formanilide (U.S. Pat. No. 3,994,974), particularly its fumarate salt is another well-known adrenoreceptor agonist which is now used clinically in the treatment of bronchial asthma and related disorders.

Although salmeterol and the other commercially available $\beta_2$-adrenoreceptor agonists are effective bronchodilators, the maximum duration of action is 12 hours, hence twice daily dosing is often required. There is therefore a clinical need for compounds having potent and selective stimulant action at $\beta_2$-adrenoreceptors and having an advantageous profile of action.

According to the present invention, there is provided a compound of formula (I)

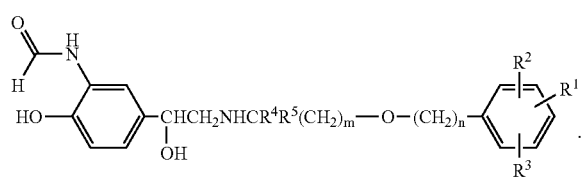
(I)

or a salt, solvate, or physiologically functional derivative thereof, wherein:
m is an integer of from 2 to 8;
n is an integer of from 3 to 11, preferably from 3 to 7;
with the proviso that m+n is 5 to 19, preferably 5 to 12;
$R^1$ is —$XSO_2NR^6R^7$
  wherein X is —$(CH_2)_p$— or $C_{2-6}$ alkenylene;
  $R^6$ and $R^7$ are independently selected from hydrogen, $C_{1-6}$alkyl, $C_{3-7}$cycloalkyl, $C(O)NR^8R^9$, phenyl, and phenyl ($C_{1-4}$alkyl)-,
  or $R^6$ and $R^7$, together with the nitrogen to which they are bonded, form a 5-, 6-, or 7-membered nitrogen containing ring,
  and $R^6$ and $R^7$ are each optionally substituted by one or two groups selected from halo, $C_{1-6}$alkyl, $C_{1-6}$haloalkyl, $C_{1-6}$alkoxy, hydroxy-substituted $C_{1-6}$alkoxy, —$CO_2R^8$, —$SO_2NR^8R^9$, —$CONR^8R^9$, —$NR^8C(O)R^9$, or a 5-, 6- or 7-membered heterocylic ring;
  $R^8$ and $R^9$ are independently selected from hydrogen, $C_{1-6}$alkyl, $C_{3-6}$cycloalkyl, phenyl, and phenyl ($C_{1-4}$alkyl)-; and
  p is an integer of from 0 to 6, preferably from 0 to 4;
$R^2$ and $R^3$ are independently selected from hydrogen, $C_{1-6}$alkyl, $C_{1-6}$alkoxy, halo, phenyl, and $C_{1-6}$haloalkyl;
$R^4$ and $R^5$ are independently selected from hydrogen and $C_{1-4}$alkyl with the proviso that the total number of carbon atoms in $R^4$ and $R^5$ is not more than 4.

In the compounds of formulae (I) and $R^1$ is preferably —$SO_2NR^6R^7$ wherein $R^6$ and $R^7$ are independently selected from hydrogen and $C_{1-6}$alkyl, more preferably $R^1$ is —$SO_2NH_2$.

In the compounds of formula (I) the group $R^1$ is preferably attached to the meta-position relative to the —O—$(CH_2)_n$—, —O—$(CH_2)_4$— or —O—$(CH_2)_3$— link respectively.

In the compounds of formula (I), $R^4$ and $R^5$ are preferably independently selected from hydrogen and methyl, more preferably $R^4$ and $R^5$ are both hydrogen.

In the compounds of formula (I), m is suitably 4, 5, or 6, and preferably m is 5, and n is suitably 3, 4, 5 or 6. Preferably m is 5 or 6 and n is 3 or 4 such that m+n is 8, 9 or 10, preferably 9.

According to a preferred aspect of the invention, there is provided a compound of formula (Ia)

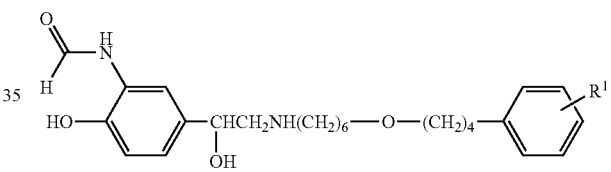
(Ia)

or a salt, solvate, or physiologically functional derivative thereof, wherein
$R^1$ is as defined above for formula (I).

According to a further preferred aspect of the invention, there is provided a compound of formula (Ib)

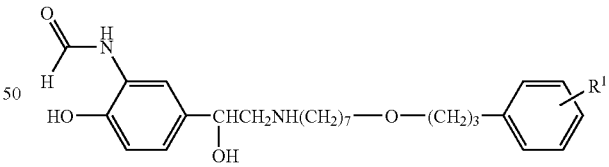
(Ib)

or a salt, solvate, or physiologically functional derivative thereof, wherein
$R^1$ is as defined above for formula (I).

In the compounds of formulae (Ia) and (Ib), $R^1$ is preferably —$SO_2NR^6R^7$ wherein $R^6$ and $R^7$ are independently selected from hydrogen and $C_{1-6}$alkyl, more preferably $R^1$ is —$SO_2NH_2$.

In the compounds of formulae (Ia) and (Ib), the group $R^1$ is preferably attached to the meta-position relative to the —O—$(CH_2)_n$—, —O—$(CH_2)_4$— or —O—$(CH_2)_3$— link respectively.

It is to be understood that the present invention covers all combinations of particular and preferred groups described hereinabove.

Preferred compounds of the invention include:

3-(4-{[6-({2-[3-(formylamino)-4-hydroxyphenyl]-2-hydroxyethyl}amino)hexyl]oxy}butyl)benzenesulfonamide; and N-(tert-butyl)-3-(4-{[6-({2-[3-(formylamino)-4-hydroxyphenyl]-2-hydroxyethyl}amino)hexyl]oxy}butyl)benzenesulfonamide;

and salts, solvates, and physiologically functional derivatives thereof.

In the definition of $R^1$, the term "5-, 6-, or 7-membered nitrogen containing ring" means a 5-, 6-, or 7-membered saturated or unsaturated ring which includes a nitrogen atom and optionally 1 or 2 other heteroatoms independently selected from nitrogen, sulphur, and oxygen. Suitable examples of such a ring include piperidinyl, morpholinyl, and piperazinyl.

In the definition of $R^1$, the term "5-, 6-, or 7-membered heterocyclic ring" means a 5-, 6-, or 7-membered saturated or unsaturated ring which includes 1, 2 or 3 heteroatoms independently selected from nitrogen, sulphur, and oxygen. Suitable examples of such a ring include piperidinyl, morpholinyl, and piperazinyl.

In the definition of X, the term "alkenylene" includes both cis and trans structures. Suitable examples of alkenylene groups include —CH═CH—.

The compounds of formulae (I), (Ia) and (Ib) include an asymmetric centre, namely the carbon atom of the

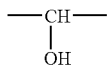

group. The present invention includes both (S) and (R) enantiomers either in substantially pure form or admixed in any proportions.

Similarly, where $R^4$ and $R^5$ are different groups, the carbon atom to which they are attached is an asymmetric centre and the present invention includes both (S) and (R) enantiomers at this centre either in substantially pure form or admixed in any proportions.

Thus the compounds of formulae (I), (Ia) and (Ib) include all enantiomers and diastereoisomers as well as mixtures thereof in any proportions.

Particularly preferred compounds of the invention include:

3-(4-{[6-({(2R)-2-[3-(formylamino)-4-hydroxyphenyl]-2-hydroxyethyl}amino)hexyl]oxy}butyl)benzenesulfonamide;

3-(4-{[6-({(2S)-2-[3-(formylamino)-4-hydroxyphenyl]-2-hydroxyethyl}amino)hexyl]oxy}butyl)benzenesulfonamide;

3-(4-{[6-({(2R/S)-2-[3-(formylamino)-4-hydroxyphenyl]-2-hydroxyethyl}amino)hexyl]oxy}butyl)benzenesulfonamide;

N-(tert-butyl)-3-(4-{[6-({(2R)-2-[3-(formylamino)-4-hydroxyphenyl]-2-hydroxyethyl}amino)hexyl]oxy}butyl)benzenesulfonamide;

N-(tert-butyl)-3-(4-{[6-({(2S)-2-[3-(formylamino)-4-hydroxyphenyl]-2-hydroxyethyl}amino)hexyl]oxy}butyl)benzenesulfonamide;

N-(tert-butyl)-3-(4-{[6-({(2R/S)-2-[3-(formylamino)-4-hydroxyphenyl]-2-hydroxyethyl}amino)hexyl]oxy}butyl)benzenesulfonamide;

and salts, solvates, and physiologically functional derivatives thereof.

Salts and solvates of compounds of formulae (I), (Ia) and (Ib) which are suitable for use in medicine are those wherein the counterion or associated solvent is pharmaceutically acceptable. However, salts and solvates having non-pharmaceutically acceptable counterions or associated solvents are within the scope of the present invention, for example, for use as intermediates in the preparation of other compounds of formulae (I), (Ia) and (Ib) and their pharmaceutically acceptable salts, solvates, and physiologically functional derivatives.

By the term physiologically functional derivative is meant a chemical derivative of a compound of formula (I), (Ia) or (Ib) having the same physiological function as the free compound of formula (I), (Ia) or (Ib), for example, by being convertible in the body thereto. According to the present invention, examples of physiologically functional derivatives include esters.

Suitable salts according to the invention include those formed with both organic and inorganic acids or bases. Pharmaceutically acceptable acid addition salts include those formed from hydrochloric, hydrobromic, sulphuric, citric, tartaric, phosphoric, lactic, pyruvic, acetic, trifluoroacetic, triphenylacetic, sulphamic, sulphanilic, succinic, oxalic, fumaric, maleic, malic, glutamic, aspartic, oxaloacetic, methanesulphonic, ethanesulphonic, arylsulponic (for example p-toluenesulphonic, benzenesulphonic, naphthalenesulphonic or naphthalenedisulphonic), salicylic, glutaric, gluconic, tricarballylic, cinnamic, substituted cinnamic (for example, methyl, methoxy or halo substituted cinnamic, including 4-methyl and 4-methoxycinnamic acid), ascorbic, oleic, naphthoic, hydroxynaphthoic (for example 1- or 3-hydroxy-2-naphthoic), naphthaleneacrylic (for example naphthalene-2-acrylic), benzoic, 4-methoxybenzoic, 2- or 4-hydroxybenzoic, 4-chlorobenzoic, 4-phenylbenzoic, bezeneacrylic (for example 1,4-benzenediacrylic) and isethionic acids. Pharmaceutically acceptable base salts include ammonium salts, alkali metal salts such as those of sodium and potassium, alkaline earth metal salts such as those of calcium and magnesium and salts with organic bases such as dicyclohexyl amine and N-methyl-D-glucamine.

Pharmaceutically acceptable esters of the compounds of formulae (I), (Ia) and (Ib) may have a hydroxyl group converted to a $C_{1-6}$alkyl, aryl, aryl $C_{1-6}$ alkyl, or amino acid ester.

As mentioned above, the compounds of formulae (I), (Ia) and (Ib) are selective $\beta_2$-adrenoreceptor agonists as demonstrated using functional or reporter gene readout from cell lines transfected with human beta-adrenoreceptors as described below. Compounds according to the present invention also have the potential to combine long duration of effect with rapid onset of action. Furthermore, certain compounds have shown an improved therapeutic index in animal models relative to existing long-acting $\beta_2$-agonist bronchodilators. As such, compounds of the invention may be suitable for once-daily administration.

Therefore, compounds of formulae (I), (Ia) and (Ib) and their pharmaceutically acceptable salts, solvates, and physiologically functional derivatives have use in the prophylaxis and treatment of clinical conditions for which a selective $\beta_2$-adrenoreceptor agonist is indicated. Such conditions include diseases associated with reversible airways obstruction such as asthma, chronic obstructive pulmonary diseases (COPD) (e.g. chronic and wheezy bronchitis, emphysema), respiratory tract infection and upper respiratory tract disease (e.g. rhinitis, including seasonal and allergic rhinitis).

Other conditions which may be treated include premature labour, depression, congestive heart failure, skin diseases (e.g. inflammatory, allergic, psoriatic, and proliferative skin diseases), conditions where lowering peptic acidity is desirable (e.g. peptic and gastric ulceration) and muscle wasting disease.

Accordingly, the present invention provides a method for the prophylaxis or treatment of a clinical condition in a mammal, such as a human, for which a selective $\beta_2$-adrenoreceptor agonist is indicated, which comprises administration of a therapeutically effective amount of a compound of formula (I), (Ia) or (Ib), or a pharmaceutically acceptable salt, solvate, or physiologically functional derivative thereof. In particular, the present invention provides such a method for the prophylaxis or treatment of a disease associated with reversible airways obstruction such as asthma, chronic obstructive pulmonary disease (COPD), respiratory tract infection or upper respiratory tract disease. In a further aspect the present invention provides such a method for the prophylaxis or treatment of a clinical condition selected from premature labour, depression, congestive heart failure, skin diseases (e.g. inflammatory, allergic, psoriatic, and proliferative skin diseases), conditions where lowering peptic acidity is desirable (e.g. peptic and gastric ulceration) or muscle wasting disease.

In the alternative, there is also provided a compound of formula (I), (Ia) or (Ib) or a pharmaceutically acceptable salt, solvate, or physiologically functional derivative thereof for use in medical therapy, particularly, for use in the prophylaxis or treatment of a clinical condition in a mammal, such as a human, for which a selective $\beta_2$-adrenoreceptor agonist is indicated. In particular, there is provided a compound of formula (I), (Ia) or (Ib) or a pharmaceutically acceptable salt, solvate, or physiologically functional derivative thereof for the prophylaxis or treatment of a disease associated with reversible airways obstruction such as asthma, chronic obstructive pulmonary disease (COPD), respiratory tract infection or upper respiratory tract disease. In a further aspect, there is provided a compound of formula (I), (Ia) or (Ib) or a pharmaceutically acceptable salt, solvate, or physiologically functional derivative thereof for the prophylaxis or treatment of a clinical condition selected from premature labour, depression, congestive heart failure, skin diseases (e.g. inflammatory, allergic, psoriatic, and proliferative skin diseases), conditions where lowering peptic acidity is desirable (e.g. peptic and gastric ulceration) or muscle wasting disease.

The present invention also provides the use of a compound of formula (I), (Ia) or (Ib), or a pharmaceutically acceptable salt, solvate, or physiologically functional derivative thereof in the manufacture of a medicament for the prophylaxis or treatment of a clinical condition for which a selective $\beta_2$-adrenoreceptor agonist is indicated, for example a disease associated with reversible airways obstruction such as asthma, chronic obstructive pulmonary disease (COPD), respiratory tract infection or upper respiratory tract disease. In a further aspect, there is provided a compound of formula (I), (Ia) or (Ib), or a pharmaceutically acceptable salt, solvate, or physiologically functional derivative thereof in the manufacture of a medicament for the prophylaxis or treatment of a clinical condition selected from premature labour, depression, congestive heart failure, skin diseases (e.g. inflammatory, allergic, psoriatic, and proliferative skin diseases), conditions where lowering peptic acidity is desirable (e.g. peptic and gastric ulceration) and muscle wasting disease.

The amount of a compound of formula (I), (Ia) or (Ib), or a pharmaceutically acceptable salt, solvate or physiologically functional derivative thereof which is required to achieve a therapeutic effect will, of course, vary with the particular compound, the route of administration, the subject under treatment, and the particular disorder or disease being treated. The compounds of the invention may be administered by inhalation at a dose of from 0.0005 mg to 10 mg, preferably 0.005 mg to 0.5 mg. The dose range for adult humans is generally from 0.0005 mg to 100 mg per day and preferably 0.01 mg to 1 mg per day.

While it is possible for the compound of formula (I), (Ia) or (Ib), or a pharmaceutically acceptable salt, solvate, or physiologically functional derivative thereof to be administered alone, it is preferable to present it as a pharmaceutical formulation.

Accordingly, the present invention further provides a pharmaceutical formulation comprising a compound of formula (I), (Ia) or (Ib) or a pharmaceutically acceptable salt, solvate, or physiologically functional derivative thereof, and a pharmaceutically acceptable carrier or excipient, and optionally one or more other therapeutic ingredients.

Hereinafter, the term "active ingredient" means a compound of formula (I), (Ia) or (Ib), or a pharmaceutically acceptable salt, solvate, or physiologically functional derivative thereof.

The formulations include those suitable for oral, parenteral (including subcutaneous, intradermal, intramuscular, intravenous and intraarticular), intranasal, inhalation (including fine particle dusts or mists which may be generated by means of various types of metered dose pressurised aerosols, nebulisers or insufflators), rectal and topical (including dermal, buccal, sublingual and intraocular) administration although the most suitable route may depend upon for example the condition and disorder of the recipient. The formulations may conveniently be presented in unit dosage form and may be prepared by any of the methods well known in the art of pharmacy. All methods include the step of bringing the active ingredient into association with the carrier which constitutes one or more accessory ingredients. In general the formulations are prepared by uniformly and intimately bringing into association the active ingredient with liquid carriers or finely divided solid carriers or both and then, if necessary, shaping the product into the desired formulation.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or moulding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein.

Formulations for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilised) condition requiring only the addition of the sterile liquid carrier, for example saline or water-for-injection, immediately prior to use. Extemporaneous injection solutions and suspensions may be prepared from sterile powders, granules and tablets of the kind previously described.

Dry powder compositions for topical delivery to the lung by inhalation may, for example, be presented in capsules and cartridges of for example gelatine, or blisters of for example laminated aluminium foil, for use in an inhaler or insufflator. Formulations generally contain a powder mix for inhalation of the compound of the invention and a suitable powder base (carrier substance) such as lactose or starch. Use of lactose is preferred. Each capsule or cartridge may generally contain between 20 µg–10 mg of the compound of formula (I) optionally in combination with another therapeutically active ingredient. Alternatively, the compound of the invention may be presented without excipients. Packaging of the formulation may be suitable for unit dose or multi-dose delivery. In the case of multi-dose delivery, the formulation can be pre-metered (eg as in Diskus, see GB 2242134 or Diskhaler, see GB 2178965, 2129691 and 2169265) or metered in use (eg as in Turbuhaler, see EP 69715). An example of a unit-dose device is Rotahaler (see GB 2064336). The Diskus inhalation device comprises an elongate strip formed from a base sheet having a plurality of recesses spaced along its length and a lid sheet hermetically but peelably sealed thereto to define a plurality of containers, each container having therein an inhalable formulation containing a compound of formula (I) preferably combined with lactose. Preferably, the strip is sufficiently flexible to be wound into a roll. The lid sheet and base sheet will preferably have leading end portions which are not sealed to one another and at least one of the said leading end portions is constructed to be attached to a winding means. Also, preferably the hermetic seal between the base and lid sheets extends over their whole width. The lid sheet may preferably be peeled from the base sheet in a longitudinal direction from a first end of the said base sheet.

Spray compositions for topical delivery to the lung by inhalation may for example be formulated as aqueous solutions or suspensions or as aerosols delivered from pressurised packs, such as a metered dose inhaler, with the use of a suitable liquefied propellant. Aerosol compositions suitable for inhalation can be either a suspension or a solution and generally contain the compound of formula (I) optionally in combination with another therapeutically active ingredient and a suitable propellant such as a fluorocarbon or hydrogen-containing chlorofluorocarbon or mixtures thereof, particularly hydrofluoroalkanes, e.g. dichlorodifluloromethane, trichlorofluoromethane, dichlorotetra-fluoroethane, especially 1,1,1,2-tetrafluoroethane, 1,1,1,2,3,3,3-heptafluoro-n-propane or a mixture thereof. Carbon dioxide or other suitable gas may also be used as propellant. The aerosol composition may be excipient free or may optionally contain additional formulation excipients well known in the art such as surfactants eg oleic acid or lecithin and cosolvents eg ethanol. Pressurised formulations will generally be retained in a canister (eg an aluminium canister) closed with a valve (eg a metering valve) and fitted into an actuator provided with a mouthpiece.

Medicaments for administration by inhalation desirably have a controlled particle size. The optimum particle size for inhalation into the bronchial system is usually 1–10 µm, preferably 2–5 µm. Particles having a size above 20 µm are generally too large when inhaled to reach the small airways. To achieve these particle sizes the particles of the active ingredient as produced may be size reduced by conventional means eg by micronisation. The desired fraction may be separated out by air classification or sieving. Preferably, the particles will be crystalline. When an excipient such as lactose is employed, generally, the particle size of the excipient will be much greater than the inhaled medicament within the present invention. When the excipient is lactose it will typically be present as milled lactose, wherein not more than 85% of lactose particles will have a MMD of 60–90 µm and not less than 15% will have a MMD of less than 15 µm.

Solutions for inhalation by nebulation may be formulated with an aqueous vehicle with the addition of agents such as acid or alkali, buffer salts, isotonicity adjusting agents or antimicrobials. They may be sterilised by filtration or heating in an autoclave, or presented as a non-sterile product.

Formulations for rectal administration may be presented as a suppository with the usual carriers such as cocoa butter or polyethylene glycol.

Formulations for topical administration in the mouth, for example buccally or sublingually, include lozenges comprising the active ingredient in a flavoured basis such as sucrose and acacia or tragacanth, and pastilles comprising the active ingredient in a basis such as gelatin and glycerin or sucrose an acacia.

Preferred unit dosage formulations are those containing an effective dose, as hereinbefore recited, or an appropriate fraction thereof, of the active ingredient.

It should be understood that in addition to the ingredients particularly mentioned above, the formulations of this invention may include other agents conventional in the art having regard to the type of formulation in question, for example those suitable for oral administration may include flavouring agents.

The compounds and pharmaceutical formulations according to the invention may be used in combination with or include one or more other therapeutic agents, for example anti-inflammatory agents, anticholinergic agents (particularly an $M_1$, $M_2$, $M_1/M_2$ or $M_3$ receptor antagonist), other $\beta_2$-adrenoreceptor agonists, antiinfective agents (e.g. antibiotics, antivirals), or antihistamines. The invention thus provides, in a further aspect, a combination comprising a compound of formula (I) or a pharmaceutically acceptable salt, solvate or physiologically functional derivative thereof together with one or more other therapeutically active agents, for example, an anti-inflammatory agent (for example a corticosteroid or an NSAID), an anticholinergic agent, another $\beta_2$-adrenoreceptor agonist, an antiinfective agent (e.g. an antibiotic or an antiviral), or an antihistamine. Preferred are combinations comprising a compound of formula (I) or a pharmaceutically acceptable salt, solvate or physiologically functional derivative thereof together with a corticosteroid, and/or an anticholinergic, and/or a PDE-4 inhibitor. Preferred combinations are those comprising one or two other therapeutic agents.

It will be clear to a person skilled in the art that, where appropriate, the other therapeutic ingredient(s) may be used in the form of salts, (e.g. as alkali metal or amine salts or as acid addition salts), or prodrugs, or as esters (e.g. lower alkyl esters), or as solvates (e.g. hydrates) to optimise the activity and/or stability and/or physical characteristics (e.g. solubility) of the therapeutic ingredient. It will be clear also that where appropriate, the therapeutic ingredients may be used in optically pure form.

Suitable anti-inflammatory agents include corticosteroids and NSAIDs. Suitable corticosteroids which may be used in combination with the compounds of the invention are those oral and inhaled corticosteroids and their pro-drugs which have anti-inflammatory activity. Examples include methyl prednisolone, prednisolone, dexamethasone, fluticasone propionate, 6α,9α-difluoro-17α-[(2-furanylcarbonyl)oxy]-11β-hydroxy-16α-methyl-3-oxo-androsta-1,4-diene-17β-carbothioic acid S-fluoromethyl ester, 6α,9α-difluoro-11β-hydroxy-16α-methyl-3-oxo-17α-propionyloxy-androsta-1,4-diene-17β-carbothioic acid S-(2-oxo-tetrahydro-furan-3S-yl) ester, beclomethasone esters (e.g. the 17-propionate ester or the 17,21-dipropionate ester), budesonide, flunisolide, mometasone esters (e.g. the furoate ester), triamcinolone acetonide, rofleponide, ciclesonide, butixocort propionate, RPR-106541, and ST-126. Preferred corticosteroids include fluticasone propionate, 6α,9α-difluoro-11β-hydroxy-16α-methyl-17α-[(4-methyl-1,3-thiazole-5-carbonyl)oxy]-3-oxo-androsta-1,4-diene-17β-carbothioic acid S-fluoromethyl ester and 6α,9α-difluoro-17α-[(2-furanylcarbonyl)oxy]-11β-hydroxy-16α-methyl-3-oxo-androsta-1,4-diene-17β-carbothioic acid S-fluoromethyl ester, more preferably 6α,9α-difluoro-17α-[(2-furanylcarbonyl)oxy]-11β-hydroxy-16α-methyl-3-oxo-androsta-1,4-diene-17β-carbothioic acid S-fluoromethyl ester.

Suitable NSAIDs include sodium cromoglycate, nedocromil sodium, phosphodiesterase (PDE) inhibitors (e.g. theophylline, PDE4 inhibitors or mixed PDE3/PDE4 inhibitors), leukotriene antagonists, inhibitors of leukotriene synthesis, iNOS inhibitors, tryptase and elastase inhibitors, beta-2 integrin antagonists and adenosine receptor agonists or antagonists (e.g. adenosine 2a agonists), cytokine antagonists (e.g. chemokine antagonists) or inhibitors of cytokine synthesis. Suitable other β$_2$-adrenoreceptor agonists include salmeterol (e.g. as the xinafoate), salbutamol (e.g. as the sulphate or the free base), formoterol (e.g. as the fumarate), fenoterol or terbutaline and salts thereof.

Of particular interest is use of the compound of formula (I) in combination with a phosphodiesterase 4 (PDE4) inhibitor or a mixed PDE3/PDE4 inhibitor. The PDE4-specific inhibitor useful in this aspect of the invention may be any compound that is known to inhibit the PDE4 enzyme or which is discovered to act as a PDE4 inhibitor, and which are only PDE4 inhibitors, not compounds which inhibit other members of the PDE family as well as PDE4. Generally it is preferred to use a PDE4 inhibitor which has an IC$_{50}$ ratio of about 0.1 or greater as regards the IC$_{50}$ for the PDE4 catalytic form which binds rolipram with a high affinity divided by the IC$_{50}$ for the form which binds rolipram with a low affinity. For the purposes of this disclosure, the cAMP catalytic site which binds R and S rolipram with a low affinity is denominated the "low affinity" binding site (LPDE 4) and the other form of this catalytic site which binds rolipram with a high affinity is denominated the "high affinity" binding site (HPDE 4). This term "HPDE4" should not be confused with the term "hPDE4" which is used to denote human PDE4. Initial experiments were conducted to establish and validate a [$^3$H]-rolipram binding assay. Details of this work are given in the Binding Assays described in detail below.

The preferred PDE4 inhibitors of use in this invention will be those compounds which have a salutary therapeutic ratio, i.e., compounds which preferentially inhibit cAMP catalytic activity where the enzyme is in the form that binds rolipram with a low affinity, thereby reducing the side effects which apparently are linked to inhibiting the form which binds rolipram with a high affinity. Another way to state this is that the preferred compounds will have an IC$_{50}$ ratio of about 0.1 or greater as regards the IC$_{50}$ for the PDE4 catalytic form which binds rolipram with a high affinity divided by the IC$_{50}$ for the form which binds rolipram with a low affinity.

A further refinement of this standard is that of one wherein the PDE4 inhibitor has an IC$_{50}$ ratio of about 0.1 or greater; said ratio is the ratio of the IC$_{50}$ value for competing with the binding of 1 nM of [$^3$H]R-rolipram to a form of PDE4 which binds rolipram with a high affinity over the IC$_{50}$ value for inhibiting the PDE4 catalytic activity of a form which binds rolipram with a low affinity using 1 μM[$^3$H]-cAMP as the substrate.

Examples of useful PDE4 inhibitors are:
(R)-(+)-1-(4-bromobenzyl)-4-[(3-cyclopentyloxy)-4-methoxyphenyl]-2-pyrrolidone;
(R)-(+)-1-(4-bromobenzyl)-4-[(3-cyclopentyloxy)-4-methoxyphenyl]-2-pyrrolidone;
3-(cyclopentyloxy-4-methoxyphenyl)-1-(4-N'-[N2-cyano-S-methyl-isothioureido]benzyl)-2-pyrrolidone;
cis 4-cyano-4-(3-cyclopentyloxy-4-methoxyphenyl)cyclohexan-1-carboxylic acid];
cis-[4-cyano-4-(3-cyclopropylmethoxy-4-difluoromethoxyphenyl)cyclohexan-1-ol];
(R)-(+)-ethyl[4-(3-cyclopentyloxy-4-methoxyphenyl)pyrrolidine-2-ylidene]acetate; and
(S)-(−)-ethyl[4-(3-cyclopentyloxy-4-methoxyphenyl)pyrrolidine-2-ylidene]acetate.

Most preferred are those PDE4 inhibitors which have an IC$_{50}$ ratio of greater than 0.5, and particularly those compounds having a ratio of greater than 1.0. Preferred compounds are cis 4-cyano-4-(3-cyclopentyloxy-4-methoxyphenyl)cyclohexan-1-carboxylic acid, 2-carbomethoxy-4-cyano-4-(3-cyclopropylmethoxy-4-difluoromethoxyphenyl)cyclohexan-1-one and cis-[4-cyano-4-(3-cyclopropylmethoxy-4-difluoromethoxyphenyl)cyclohexan-1-ol]; these are examples of compounds which bind preferentially to the low affinity binding site and which have an IC$_{50}$ ratio of 0.1 or greater.

Other compounds of interest include:
Compounds set out in U.S. Pat. No. 5,552,438 issued 3 Sep. 1996; this patent and the compounds it discloses are incorporated herein in full by reference. The compound of particular interest, which is disclosed in U.S. Pat. No. 5,552,438, is cis-4-cyano-4-[3-(cyclopentyloxy)-4-methoxyphenyl]cyclohexane-1-carboxylic acid (also known as cilomalast) and its salts, esters, pro-drugs or physical forms; AWD-12-281 from Asta Medica (Hofgen, N. et al. 15th EFMC Int Symp Med Chem (September 6–10, Edinburgh) 1998, Abst P.98; CAS reference No. 247584020-9); a 9-benzyladenine derivative nominated NCS-613 (INSERM); D-4418 from Chiroscience and Schering-Plough; a benzodiazepine PDE4 inhibitor identified as CI-1018 (PD-168787) and attributed to Pfizer; a benzodioxole derivative disclosed by Kyowa Hakko in WO99/16766; K-34 from Kyowa Hakko; V-11294A from Napp (Landells, L. J. et al. Eur Resp J [Annu Cong Eur Resp Soc (September 19–23, Geneva) 1998] 1998, 12 (Suppl. 28): Abst P2393); roflumilast (CAS reference No 162401-32-3) and a pthalazinone (WO99/47505, the disclosure of which is hereby incorporated by reference) from Byk-Gulden; Pumafentrine, (−)-p-[(4aR*,10bS*)-9-ethoxy-1,2,3,4,4a,10b-hexahydro-8-methoxy-2-methylbenzo[c][1,6]naphthyridin-6-yl]-N,N-diisopropylbenzamide which is a mixed PDE3/PDE4 inhibitor which has been prepared and published on by Byk-Gulden, now Altana; arofylline under development by Almirall-Prodesfarma; VM554/UM565 from Vemalis; or T-440 (Tanabe Seiyaku; Fuji, K. et al. J Pharmacol Exp Ther, 1998, 284(1): 162), and T2585.

Other possible PDE-4 and mixed PDE3/PDE4 inhibitors include those listed in WO01/13953, the disclosure of which is hereby incorporated by reference.

Phosphodiesterase and Rolipram Binding Assays

Assay Method 1A

Isolated human monocyte PDE4 and hrPDE (human recombinant PDE4) was determined to exist primarily in the low affinity form. Hence, the activity of test compounds against the low affinity form of PDE4 can be assessed using standard assays for PDE4 catalytic activity employing 1 µM [$^3$H]cAMP as a substrate (Torphy et al., J. of Biol. Chem., Vol. 267, No. 3 pp1798–1804, 1992). Rat brain high speed supernatants were used as a source of protein and both enantiomers of [$^3$H]-rolipram were prepared to a specific activity of 25.6 Ci/mmol. Standard assay conditions were modified from the published procedure to be identical to the PDE assay conditions, except for the last of the cAMP: 50 mM Tris HCl (pH 7.5), 5 mM $MgCl_2$, 50 µM 5'-AMP and 1 nM of [$^3$H]-rolipram (Torphy et al., J. of Biol. Chem., Vol. 267, No. 3 pp1798–1804, 1992). The assay was run for 1 hour at 30° C. The reaction was terminated and bound ligand was separated from free ligand using a Brandel cell harvester. Competition for the high affinity binding site was assessed under conditions that were identical to those used for measuring low affinity PDE activity, expect that [$^3$H]-cAMP was not present.

Assay Method 1B

Measurement of Phosphodiesterase Activity

PDE activity was assayed using a [$^3$H]cAMP SPA or [$^3$H]cGMP SPA enzyme assay as described by the supplier (Amersham Life Sciences). The reactions were conducted in 96-well plates at room temperature, in 0.1 ml of reaction buffer containing (final concentrations): 50 mM Tris-HCl, pH 7.5, 8.3 mM $MgCl_2$, 1.7 mM EGTA, [$^3$H]cAMP or [$^3$H]cGMP (approximately 2000 dpm/pmol), enzyme and various concentrations of the inhibitors. The assay was allowed to proceed for 1 hr and was terminated by adding 50 µl of SPA yttrium silicate beads in the presence of zinc sulfate. The plates were shaken and allowed to stand at room temperature for 20 min. Radiolabeled product formation was assessed by scintillation spectrometry.

[$^3$H]R-rolipram Binding Assay

The [$^3$H]R-rolipram binding assay was performed by modification of the method of Schneider and co-workers, see Nicholson, et al., Trends Pharmacol. Sci., Vol. 12, pp.19–27 (1991) and McHale et al., Mol. Pharmacol., Vol. 39, 109–113 (1991). R-Rolipram binds to the catalytic site of PDE4 see Torphy et al., Mol. Pharmacol., Vol. 39, pp. 376–384 (1991). Consequently, competition for [$^3$H]R-rolipram binding provides an independent confirmation of the PDE4 inhibitor potencies of unlabeled competitors. The assay was performed at 30° C. for 1 hr in 0.5 µl buffer containing (final concentrations): 50 mM Tris-HCl, pH 7.5, 5 mM $MgCl_2$, 0.05% bovine serum albumin, 2 nM [$^3$H]R-rolipram (5.7×104 dpm/pmol) and various concentrations of non-radiolabeled inhibitors. The reaction was stopped by the addition of 2.5 ml of ice-cold reaction buffer (without [$^3$H]-R-rolipram) and rapid vacuum filtration (Brandel Cell Harvester) through Whatman GF/B filters that had been soaked in 0.3% polyethylenimine. The filters were washed with an additional 7.5 ml of cold buffer, dried, and counted via liquid scintillation spectrometry.

Suitable anticholinergic agents are those compounds that act as antagonists at the muscarinic receptor, in particular those compounds which are antagonists of the $M_1$ and $M_2$ receptors. Exemplary compounds include the alkaloids of the belladonna plants as illustrated by the likes of atropine, scopolamine, homatropine, hyoscyamine; these compounds are normally administered as a salt, being tertiary amines. These drugs, particularly the salt forms, are readily available from a number of commercial sources or can be made or prepared from literature data via, to wit:

Atropine—CAS-51-55-8 or CAS-51-48-1 (anhydrous form), atropine sulfate—CAS-5908-99-6; atropine oxide—CAS-4438-22-6 or its HCl salt—CAS-4574-60-1 and methylatropine nitrate—CAS-52-88-0.

Homatropine—CAS-87-00-3, hydrobromide salt—CAS-51-56-9, methylbromide salt—CAS-80-49-9.

Hyoscyamine (d, l)—CAS-101-31-5, hydrobromide salt—CAS-306-03-6 and sulfate salt—CAS-6835-16-1.

Scopolamine—CAS-51-34-3, hydrobromide salt—CAS-6533-68-2, methylbromide salt—CAS-155-41-9.

Preferred anticholinergics include ipratropium (e.g. as the bromide), sold under the name Atrovent, oxitropium (e.g. as the bromide) and tiotropium (e.g. as the bromide) (CAS-139404-48-1). Also of interest are: methantheline (CAS-53-46-3), propantheline bromide (CAS-50-34-9), anisotropine methyl bromide or Valpin 50 (CAS-80-50-2), clidinium bromide (Quarzan, CAS-3485-62-9), copyrrolate (Robinul), isopropamide iodide (CAS-71-81-8), mepenzolate bromide (U.S. Pat. No. 2,918,408), tridihexethyl chloride (Pathllone, CAS-4310-35-4), and hexocyclium methylsulfate (Tral, CAS-115-63-9). See also cyclopentolate hydrochloride (CAS-5870-29-1), tropicamide (CAS-1508-75-4), trihexyphenidyl hydrochloride (CAS-144-11-6), pirenzepine (CAS-29868-97-1), telenzepine (CAS-80880-90-9), AF-DX 116, or methoctramine, and the compounds disclosed in WO01/04118, the disclosure of which is hereby incorporated by reference.

Suitable antihistamines (also referred to as $H_1$-receptor antagonists) include any one or more of the numerous antagonists known which inhibit $H_1$-receptors, and are safe for human use. All are reversible, competitive inhibitors of the interaction of histamine with $H_1$-receptors. The majority of these inhibitors, mostly first generation antagonists, have a core structure, which can be represented by the following formula:

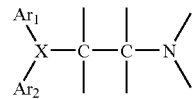

This generalized structure represents three types of antihistamines generally available: ethanolamines, ethylenediamines, and alkylamines. In addition, other first generation antihistamines include those which can be characterized as based on piperizine and phenothiazines. Second generation antagonists, which are non-sedating, have a similar structure-activity relationship in that they retain the core ethylene group (the alkylamines) or mimic the tertiary amine group with piperizine or piperidine. Exemplary antagonists are as follows:

Ethanolamines: carbinoxamine maleate, clemastine fumarate, diphenylhydramine hydrochloride, and dimenhydrinate.

Ethylenediamines: pyrilamine amleate, tripelennamine HCl, and tripelennamine citrate.

Alkylamines: chlropheniramine and its salts such as the maleate salt, and acrivastine.

Piperazines: hydroxyzine HCl, hydroxyzine pamoate, cyclizine HCl, cyclizine lactate, meclizine HCl, and cetirizine HCl.

Piperidines: Astemizole, levocabastine HCl, loratadine or its descarboethoxy analogue, and terfenadine and fexofenadine hydrochloride or another pharmaceutically acceptable salt.

Azelastine hydrochloride is yet another $H_1$ receptor antagonist which may be used in combination with a PDE4 inhibitor.

Examples of preferred anti-histamines include methapyrilene and loratadine.

The invention thus provides, in a further aspect, a combination comprising a compound of formula (I) a pharmaceutically acceptable salt, solvate or physiologically functional derivative thereof together with a PDE4 inhibitor.

The invention thus provides, in a further aspect, a combination comprising a compound of formula (I) a pharmaceutically acceptable salt, solvate or physiologically functional derivative thereof together with a corticosteroid.

The invention thus provides, in a further aspect, a combination comprising a compound of formula (I) a pharmaceutically acceptable salt, solvate or physiologically functional derivative thereof together with an anticholinergic.

The invention thus provides, in a further aspect, a combination comprising a compound of formula (I) a pharmaceutically acceptable salt, solvate or physiologically functional derivative thereof together with an antihistamine.

The invention thus provides, in a further aspect, a combination comprising a compound of formula (I) a pharmaceutically acceptable salt, solvate or physiologically functional derivative thereof together with a PDE4 inhibitor and a corticosteroid.

The invention thus provides, in a further aspect, a combination comprising a compound of formula (I) a pharmaceutically acceptable salt, solvate or physiologically functional derivative thereof together with an anticholinergic and a PDE-4 inhibitor.

The combinations referred to above may conveniently be presented for use in the form of a pharmaceutical formulation and thus pharmaceutical formulations comprising a combination as defined above together with a physiologically acceptable diluent or carrier represent a further aspect of the invention.

The individual compounds of such combinations may be administered either sequentially or simultaneously in separate or combined pharmaceutical formulations. Appropriate doses of known therapeutic agents will be readily appreciated by those skilled in the art.

According to a further aspect of the invention, there is provided a process for preparing a compound of formula (I), (Ia) or (Ib) or a salt, solvate, or physiologically functional derivative thereof which comprises a process as defined below followed by the following steps in any order:

(i) optional removal of any protecting groups,;
(ii) optional separation of an enantiomer from a mixture of enantiomers;
(iii) optional conversion of the product to a corresponding salt, solvate, or physiologically functional derivative thereof.

In one general process, a compound of formula (I), (Ia) or (Ib) may be obtained by deprotection of a protected intermediate, for example of formula (II):

(II)

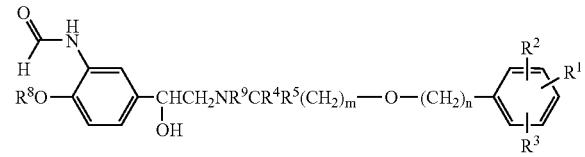

or a salt or solvate thereof, wherein $R^1$, $R^2$, $R^3$, $R^4$, $R^5$, m, and n are as defined for the compound of formula (I), (Ia) or (Ib), and $R^8$, and $R^9$ are each independently either hydrogen or a protecting group provided that at least one of $R^8$, and $R^9$ is a protecting group.

Suitable protecting groups may be any conventional protecting group such as those described in "Protective Groups in Organic Synthesis" by Theodora W Greene and Peter G M Wuts, 3rd edition (John Wiley & Sons, 1999). Examples of suitable hydroxyl protecting groups represented by $R^8$ are esters such as acetate ester, aralkyl groups such as benzyl, diphenylmethyl, or triphenylmethyl, and tetrahydropyranyl. Examples of suitable amino protecting groups represented by $R^9$ include benzyl, α-methylbenzyl, diphenylmethyl, triphenylmethyl, benzyloxycarbonyl, tert-butoxycarbonyl, and acyl groups such as trichloroacetyl or trifluoroacetyl.

As will be appreciated by the person skilled in the art, use of such protecting groups may include orthogonal protection of groups in the compounds of formula (II) to facilitate the selective removal of one group in the presence of another, thus enabling selective functionalisation of a single amino or hydroxyl function. For example; the —CH(OH) group may be orthogonally protected using, for example, a trialkylsilyl group such as triethylsilyl. A person skilled in the art will also appreciate other orthogonal protection strategies, available by conventional means as described in Theodora W Greene (see above).

The deprotection to yield a compound of formula (I), (Ia) or (Ib) may be effected using conventional techniques. Thus, for example, when $R^8$, and/or $R^9$ is an aralkyl group, this may be cleaved by hydrogenolysis in the presence of a metal catalyst (e.g. palladium on charcoal and/or palladium hydroxide on carbon).

When $R^8$ is tetrahydropyranyl this may be cleaved by hydrolysis under acidic conditions. Acyl groups represented by $R^9$ may be removed by hydrolysis, for example with a base such as sodium hydroxide, or a group such as trichloroethoxycarbonyl may be removed by reduction with, for example, zinc and acetic acid. Other deprotection methods may be found in Theodora W Greene (see above).

The enantiomeric compounds of the invention may be obtained (i) by separation of the components of the corresponding racemic mixture, for example, by means of a chiral chromatography column, enzymic resolution methods, or preparing and separating suitable diastereoisomers, or (ii) by direct synthesis from the appropriate chiral intermediates by the methods described herein.

Optional conversions of a compound of formula (I), (Ia) or (Ib) to a corresponding salt may conveniently be effected by reaction with the appropriate acid or base. Optional conversion of a compound of formula (I), (Ia) or (Ib) to a corresponding solvate or physiologically functional derivative may be effected by methods known to those skilled in the art.

Compounds of formulae (I) and (II) may be prepared from the corresponding compound of formula (III):

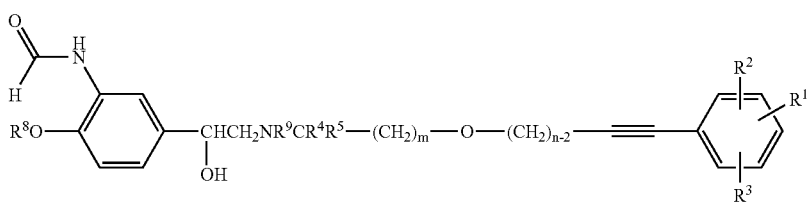

(III)

or a salt or solvate thereof, wherein $R^1$, $R^2$, $R^3$, $R^4$, $R^5$, m, and n are as defined for the compound of formula (I) or (II), and $R^8$, and $R^9$ are each independently hydrogen or a protecting group.

The conversion of a compound of formula (III) to a compound of formula (I) or (II) may be effected by reducing the triple bond. The reduction may be effected by any suitable method such as hydrogenation in the presence of a catalyst, for example, palladium/charcoal, palladium hydroxide on carbon, or platinum oxide.

If $R^8$ and/or $R^9$ is a protecting group which is cleavable by hydrogenolysis, then it may be removed under the conditions used for the reduction of the triple bond in the compound of formula (III) to give a compound of formula (I) directly or a compound of formula (II) wherein one of $R^8$ and $R^9$ is hydrogen.

Compounds of formula (III) may be prepared from the corresponding compound of formula (IV):

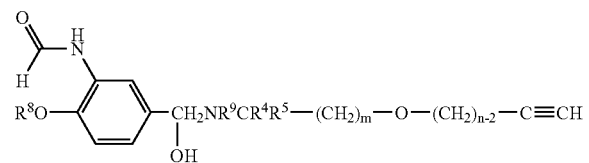

(IV)

or a salt or solvate thereof, wherein $R^4$, $R^5$, $R^8$, $R^9$, m and n are as defined for the compound of formula (III); by coupling with a compound of formula (V):

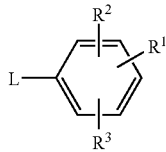

(V)

wherein $R^1$, $R^2$, and $R^3$ are as defined for the compound of formula (III) and L is a leaving group, such as a halo group (typically, bromo or iodo) or a sulphonate ester such as a haloalkyl sulphonate (typically, trifluoromethanesulphonate), or a precursor thereof (wherein one or more of the substituents $R^1$, $R^2$ or $R^3$ is a group which is convertible to the desired group $R^1$, $R^2$, or $R^3$).

The coupling of compound of formula (IV) with a compound of formula (V) is conveniently effected in the presence of a catalyst system such as bis (triphenylphosphine) palladium dichloride with cuprous iodide and an organic base such as a trialkylamine, for example, triethylamine, in a suitable solvent, for example acetonitrile or dimethylformamide.

Compounds of formula (V) are commercially available or may be prepared by methods well known to the person skilled in the art.

Compounds of formula (IV) may be prepared by coupling a compound of formula (VI):

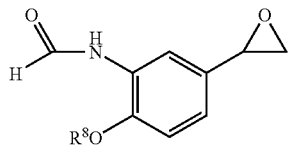

(VI)

or a salt or solvate thereof, wherein $R^8$ is as defined for the compound of formula (IV), with a compound of formula (VII):

$$NHR^9CR^4R^5(CH_2)_m\text{—}O\text{—}(CH_2)_{n\text{-}2}\text{—}C\equiv CH \qquad (VII)$$

wherein $R^4$, $R^5$, $R^9$, m and n are as defined for the compound of formula (II).

The coupling of a compound of formula (VI) with a compound of formula (VII) may be effected by simply mixing and optionally heating the compounds together, either neat or in a solvent, for example an aprotic solvent such as dimethylformamide or an alcohol such as n-butanol.

Compounds of formula (VII) may be prepared by coupling a compound of formula (VIII):

$$L^1CR^4R^5(CH_2)_m\text{—}O\text{—}(CH_2)_{n\text{-}2}\text{—}C\equiv CH \qquad (VIII)$$

wherein $R^4$, $R^5$, m and n are as defined for the compound of formula (I) and $L^1$ is a leaving group, for example a halo group (typically bromo or iodo) or a sulphonate such as an alkyl sulphonate (typically, methanesulphonate), an arylsulphonate (typically, toluenesulphonate), or a haloalkyl sulphonate (typically, trifluoromethanesulphonate), with a compound of formula (IX):

$$R^9NH_2 \qquad (IX)$$

wherein $R^9$ is as defined for the compound of formula (III).

The coupling of a compound of formula (VIII) with a compound of formula (IX) may be effected by simply mixing and optionally heating the compounds together, either neat or in an aprotic solvent, for example dimethylformamide.

Compounds of formula (VIII) may be prepared from the corresponding dihaloalkane and hydroxyalkyne by conventional chemistry, typically in the presence of an inorganic base, such as aqueous sodium hydroxide, under phase transfer conditions in the presence of a salt such as tetraalkylammonium bromide.

The compounds of formula (IX) are commercially available or may be prepared by methods well known to the person skilled in the art.

The compounds of formula (VI) are known in the art, for example in ES-A2005492 and R. Hett et al, Organic Process Research and Development, 1998, 2, 96–99, or may be prepared by methods well known to the person skilled in the art.

For a better understanding of the invention, the following Examples are given by way of illustration.

SYNTHETIC EXAMPLES

Throughout the examples, the following abbreviations are used:
LCMS: Liquid Chromatography Mass Spectrometry.
RT: retention time
THF: tetrahydofuran
DMF: N,N-dimethylformamide
bp: boiling point
ca: circa
h: hour(s)
min: minute(s)

All temperatures are given in degrees centigrade.

Silica gel refers to Merck silica gel 60 Art number 7734.

Flash silica gel refers to Merck silica gel 60 Art number 9385.

Biotage refers to prepacked silica gel cartridges containing KP-Sil run on flash 12i chromatography module.

Bond Elut are prepacked cartridges used in parallel purifications, normally under vacuum. These are commercially available from Varian.

LCMS was conducted on a Supelcosil LCABZ+PLUS column (3.3 cm×4.6 mm ID) eluting with 0.1% $HCO_2H$ and 0.01 M ammonium acetate in water (solvent A), and 0.05% $HCO_2H$ 5% water in acetonitrile (solvent B), using the following elution gradient 0–0.7 min 0% B, 0.7–4.2 min 100% B, 4.2–5.3 min 0% B, 5.3–5.5 min 0% B at a flow rate of 3 ml/min. The mass spectra were recorded on a Fisons VG Platform spectrometer using electrospray positive and negative mode (ES+ve and ES−ve).

Example 1

3-(4-{[6-({(2R)-2-[3-(Formylamino)-4-hydroxyphenyl]-2-hydroxyethyl}amino)hexyl]oxy}butyl)benzenesulfonamide compound with (2E)-but-2-enedioic acid (2:1)

i) 6-bromohexyl but-3-ynyl ether

3-Butyn-1-ol (42.4 ml) was stirred vigorously with 1,6-dibromohexane (260 ml) and tetrabutylammonium bisulphate (2.4 g) in 50% aqueous sodium hydroxide solution (200 ml) under nitrogen for 3 days. Water (ca 700 ml) was added and the organic layer was separated. The aqueous layer was extracted twice with dichloromethane (2×100 ml) and the combined organic layers were washed with water, dried ($MgSO_4$) and concentrated. The residue in petroleum ether (bp 40–60°) was loaded onto a column of silica gel (1.5 kg) and the column was eluted with petroleum ether (bp 40–60°), then 10% diethyl ether in petroleum ether (bp 40–60°) to give the title compound (103.3 g), δ ($CDCl_3$) 3.56(2H, t, J 7 Hz), 3.47(2H, t, J 7 Hz), 3.42(2H, t, J 7 Hz), 2.45(2H, m), 1.99(1H, t, J 2 Hz), 1.87(2H, m), 1.60(2H, m) and 1.50 to 1.33 (4H, m).

ii) N-Benzyl-6-(but-3-ynyloxy)hexan-1-amine

A mixture of 6-bromohexyl but-3-ynyl ether (21.5 g) and benzylamine (49.3 g) was heated at 120° for 2 h. The mixture was cooled and partitioned between 2M hydrochloric acid (40 ml) and ethyl acetate (2×200 ml). The combined extracts were washed with an aqueous sodium bicarbonate solution (100 ml), water (200 ml) and dried ($Na_2SO_4$). The solvent was removed in vacuo and the residue was purified by chromatography (Merck 9385) eluting with 2% methanol/chloroform. The appropriate fractions were evaporated to give the title compound (25.3 g). LCMS RT=2.2 min.

iii) 5-((1R)-2-{Benzyl[6-(but-3-ynyloxy)hexyl]amino}-1-hydroxyethyl)-2-(benzyloxy)phenylformamide A stirred mixture of 2-(benzyloxy-5-[(2R)-oxiran-2-yl]phenylformamide (R Hett et al, Organic Process Research & Development, 1998, 2, 96–99) (8.6 g) and N-benzyl-6-(but-3-ynyloxy)hexan-1-amine (9.1 g) was heated at 120° for 2 h. The mixture was purified by chromatography (Merck 9385) eluting with cyclohexane/ethyl acetate (2:1) to give the title compound (13.47 g). LCMS RT=2.68 min.

iv) 3-(4-{[6-(Benzyl{(2R)-2-[4-(benzyloxy)-3-(formylamino)phenyl]-2-hydroxyethyl}amino)hexyl]oxy}but-1-ynyl)benzenesulfonamide A stirred solution of 5-((1R)-2-{benzyl[6-(but-3-ynyloxy)hexyl]amino}-1-hydroxyethyl)-2-(benzyloxy)phenylformamide (500 mg) and 3-iodobenzenesulfonamide (340 mg) in acetonitrile (10 ml) and triethylamine (10 ml) with cuprous iodide (50 mg) and bis(triphenylphosphine)palladium dichloride (100 mg) was stirred at ambient temperature under nitrogen for 2 h. The mixture was evaporated in vacuo and the residue was purified by chromatography on Biotage (40 g) cartridge eluting with light petroleum 40–600/ethyl acetate (9:1) to give the title compound (330 mg). LCMS RT=3.04 min.

(v) 3-(4-{[6-({(2R)-2-[3-(Formylamino)-4-hydroxyphenyl]-2-hydroxyethyl}amino)hexyl]oxy}butyl)benzenesulfonamide compound with (2E)-but-2-enedioic acid (2:1)

A solution of 3-(4-{[6-(benzyl{(2R)-2-[4-(benzyloxy)-3-(formylamino)phenyl]-2-hydroxyethyl}amino)hexyl]oxy}but-1-ynyl)benzenesulfonamide (320 mg) in ethanol (15 ml) was hydrogenated in the presence of 10% palladium on carbon (50 mg) and palladium hydroxide on carbon (100 mg) at 100 p.s.i for 18 h. The catalyst was filtered off onto celite and the filtrate was evaporated to dryness. The residual oil was purified by chromatography on Biotage (8 g) cartridge eluting with dichloromethane/ethanol/0.88 ammonia (25:8:1). The residual oil (118 mg) was dissolved in methanol (20 ml) and treated with fumaric acid (0.5 equivalent) and evaporated to give the title compound (80 mg). LCMS RT=2.39 min, ES+ve 508 $(MH)^+$.

Example 2

N-(tert-Butyl)-3-(4-{[6-({(2R)-2-[3-(formylamino)-4-hydroxyphenyl]-2-hydroxyethyl}amino)hexyl]oxy}butyl)benzenesulfonamide i) N-(tert-Butyl)-3-iodobenzenesulfonamide tert-Butylamine (300 mg) was added to a stirred, cooled (ice-bath) solution of 3-iodobenzenesulfonyl chloride (Bromidge et al, J. Med. Chem., 1999, 42(2), 202–205) and triethylamine (420 mg) in dichloromethane (7 ml). The mixture was then stirred for 2 h at room temperature, diluted with dichloromethane (10 ml) and washed with 2M hydrochloric acid (5 ml). The mixture was separated on a hydrophobic frit and the organic phase was evaporated to give the title compound (1.26 g). LCMS ES+ve 340 $(MH)^+$.

(ii) 3-(4-{[6-(Benzyl{(2R)-2-[4-(benzyloxy)-3-(formylamino)phenyl]-2-hydroxyethyl}amino)hexyl]oxy}but-1-ynyl)-N-(tert-butyl)benzenesulfonamide was prepared by methods similar to those described in Example 1iv. TLC $SiO_2$, cyclohexane/ethyl acetate 1:1 $R_f$=0.37.

(iii) N-(tert-Butyl)-3-(4-{[6-({(2R)-2-[3-(formylamino)-4-hydroxyphenyl]-2-hydroxyethyl}amino)hexyl]oxy}butyl)benzenesulfonamide was prepared by methods similar to those described in Example 1v. LCMS RT=2.51 min, ES+ve 564 $(MH)^+$.

Biological Activity

The potencies of the aforementioned compounds were determined using frog melanophores transfected with the human beta 2 adrenoreceptor. The cells were incubated with melatonin to induce pigment aggregation. Pigment dispersal was induced by compounds acting on the human beta 2 adrenoreceptor. The beta 2 agonist activity of test compounds was assessed by their ability to induce a change in light transmittance across a melanophore monolayer (a consequence of pigment dispersal). At the human beta 2 adrenoreceptor, compounds of examples 1 and 2 had $IC_{50}$ values below 1 μM.

Potency at other beta adrenoreceptor subtypes was determined using chinese hamster ovary cells transfected with either the human beta 1 adrenoreceptor or the human beta 3 adrenoreceptor. Agonist activity was assessed by measuring changes intracellular cyclic AMP.

The application of which this description and claims forms part may be used as a basis for priority in respect of any subsequent application. The claims of such subsequent application may be directed to any feature or combination of features described herein. They may take the form of product, composition, process, or use claims and may include, by way of example and without limitation, the following claims:

What is claimed is:
1. A compound of formula (I)

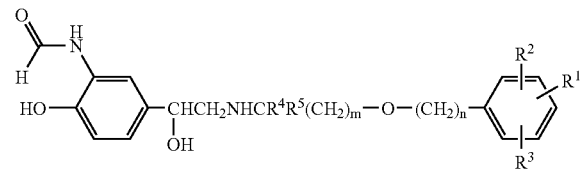

or a salt, solvate, or physiologically functional derivative thereof, wherein:
m is an integer of from 2 to 8;
n is an integer of from 3 to 11;
with the proviso that m+n is 5 to 19;
$R^1$ is $-XSO_2NR^6R^7$
wherein X is $-(CH_2)_p-$ or $C_{2-6}$ alkenylene;
$R^6$ and $R^7$ are independently selected from hydrogen, $C_{1-6}$alkyl,
$C_{3-7}$cycloalkyl, $C(O)NR^8R^9$, phenyl, and phenyl ($C_{1-4}$ alkyl)-,
or $R^6$ and $R^7$, together with the nitrogen to which they are bonded, form a 5-, 6-, or 7-membered nitrogen containing ring,
and $R^6$ and $R^7$ are each optionally substituted by one or two groups selected from halo, $C_{1-6}$alkyl, $C_{1-6}$haloalkyl, $C_{1-6}$alkoxy, hydroxy-substituted $C_{1-6}$alkoxy, $-CO_2R^8$, $-SO_2NR^8R^9$, $-CONR^8R^9$, $-NR^8C(O)R^9$,
or a 5-, 6- or 7-membered heterocylic ring;
$R^8$ and $R^9$ are independently selected from hydrogen, $C_{1-6}$alkyl,
$C_{3-6}$cycloalkyl, phenyl, and phenyl ($C_{1-4}$alkyl)-;
p is an integer of from 0 to 6;
$R^2$ and $R^3$ are independently selected from hydrogen, $C_{1-6}$alkyl, $C_{1-6}$alkoxy, halo, phenyl, and $C_{1-6}$haloalkyl;
$R^4$ and $R^5$ are independently selected from hydrogen and $C_{1-4}$alkyl with the proviso that the total number of carbon atoms in $R^4$ and $R^5$ is not more than 4.

2. A compound of according to claim 1 wherein said compound is of formula (Ia)

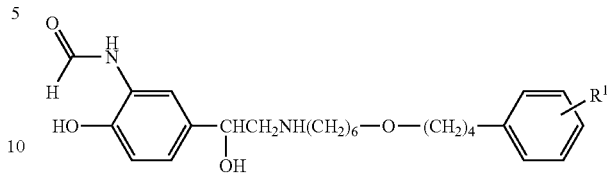

or a salt, solvate, or physiologically functional derivative thereof.

3. A compound according to claim 1 wherein said compound is of formula (Ib)

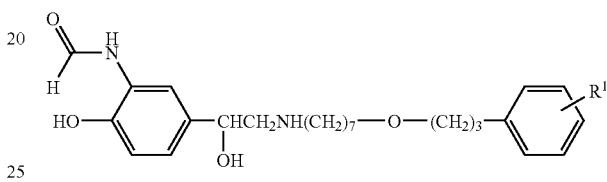

or a salt, solvate, or physiologically functional derivative thereof.

4. A compound selected from the group consisting of
3-(4-{[6-({(2R)-2-[3-(formylamino)-4-hydroxyphenyl]-2-hydroxyethyl}amino)hexyl]oxy}butyl)benzenesulfonamide;
3-(4-{[6-({(2S)-2-[3-(formylamino)-4-hydroxyphenyl]-2-hydroxyethyl}amino)hexyl]oxy}butyl)benzenesulfonamide;
3-(4-{[6-({(2R/S)-2-[3(formylamino)-4-hydroxyphenyl]-2-hydroxyethyl}amino)hexyl]oxy}butyl)benzenesulfonamide;
N-(tert-butyl)-3-(4-{[6-({(2R)-2-[3-(formylamino)-4-hydroxyphenyl]-2-hydroxyethyl}amino)hexyl]oxy}butyl)benzenesulfonamide;
N-(tert-butyl)-3-(4-{[6-({(2S)-2-[3-(formylamino)-4-hydroxyphenyl]-2-hydroxyethyl}amino)hexyl]oxy}butyl)benzenesulfonamide;
N-(tert-butyl)-3-(4-{[6-({(2R/S)-2-[3-(formylamino)-4-hydroxyphenyl]-2-hydroxyethyl}amino)hexyl]oxy}butyl)benzenesulfonamide; a salt thereof, a solvate thereof, and a physiologically functional derivative thereof.

5. A method for the prophylaxis or treatment of a clinical condition in a mammal for which a selective $\beta_2$-adrenoreceptor agonist is indicated, which comprises administration of a therapeutically effective amount of a compound according to claim 1, or a pharmaceutically acceptable salt, solvate, or physiologically functional derivative thereof.

6. A pharmaceutical formulation comprising a compound according to claim 1 or a pharmaceutically acceptable salt, solvate, or physiologically functional derivative thereof, and a pharmaceutically acceptable carrier or excipient, and optionally one or more other therapeutic ingredients.

7. A combination comprising a compound according to claim 1, or a pharmaceutically acceptable salt, solvate, or physiologically functional derivative thereof, and one or more other therapeutic ingredients.

8. A combination according to claim 7 wherein the other therapeutic ingredient is selected from the group consisting of a PDE4 inhibitor, a corticosteroid, and an anticholinergic.

9. A process for the preparation of a compound of formula (I), (Ia) or (Ib) according to any of claims 1 to 4, or a salt, solvate, or physiologically functional derivative thereof, which comprises:

(a) deprotection of a protected intermediate of formula (II):

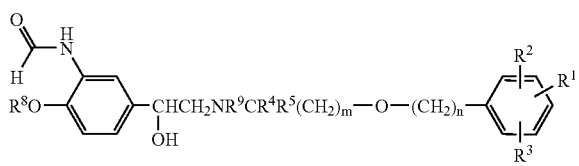

(II)

or a salt or solvate thereof, wherein $R^1$, $R^2$, $R^3$, $R^4$, $R^5$, m, and n are as defined for the compound of formula (I) in claim 1, and $R^8$, and $R^9$, are each independently either hydrogen or a protecting group provided that at least one of $R^8$, or $R^9$, is a protecting group; or (b) reduction of a compound of formula (III):

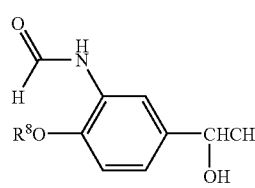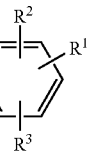

(III)

wherein $R^1$, $R^2$, $R^3$, $R^4$, $R^5$, m, and n are as defined for the compound of formula (I) in claim 1, and $R^8$, and $R^9$, are each independently either hydrogen or a protecting group;

followed by the following steps in any order:
(i) optional removal of any protecting groups;
(ii) optional separation of an enantiomer from a mixture of enantiomers;
(iii) optional conversion of the product to a corresponding salt, solvate, or physiologically functional derivative thereof.

10. A method according to claim 5, wherein the mammal is a human.

11. A method for the prophylaxis or treatment of a clinical condition in a mammal for which a selective $\beta_2$-adrenoreceptor agonist is indicated, which comprises administration of a therapeutically effective amount of a compound according to claim 2, or a pharmaceutically acceptable salt, solvate, or physiologically functional derivative thereof.

12. A method according to claim 11, wherein the mammal is a human.

13. A method for the prophylaxis or treatment of a clinical condition in a mammal for which a selective $\beta_2$-adrenoreceptor agonist is indicated, which comprises administration of a therapeutically effective amount of a compound according to claim 3, or a pharmaceutically acceptable salt, solvate, or physiologically functional derivative thereof.

14. A method according to claim 13, wherein the mammal is a human.

15. A method for the prophylaxis or treatment of a clinical condition in a mammal for which a selective $\beta_2$-adrenoreceptor agonist is indicated, which comprises administration of a therapeutically effective amount of a compound according to claim 4, or a pharmaceutically acceptable salt, solvate, or physiologically functional derivative thereof.

16. A method according to claim 15, wherein the mammal is a human.

17. A pharmaceutical formulation comprising a compound according to claim 2 or a pharmaceutically acceptable salt, solvate, or physiologically functional derivative thereof, and a pharmaceutically acceptable carrier or excipient, and optionally one or more other therapeutic ingredients.

18. A pharmaceutical formulation comprising a compound according to claim 3 or a pharmaceutically acceptable salt, solvate, or physiologically functional derivative thereof, and a pharmaceutically acceptable carrier or excipient, and optionally one or more other therapeutic ingredients.

19. A pharmaceutical formulation comprising a compound according to claim 4 or a pharmaceutically acceptable salt, solvate, or physiologically functional derivative thereof, and a pharmaceutically acceptable carrier or excipient, and optionally one or more other therapeutic ingredients.

20. A combination comprising a compound according claim 2, or a physiologically acceptable salt, solvate, or physiologically functional derivative thereof, arid one or more therapeutic ingredients.

21. A combination according to claim 20 wherein the other therapeutic ingredient is selected from the group consisting of a PDE4 inhibitor, a corticosteroid, and an anticholinergic.

22. A combination comprising a compound according to claim 3, or a physiologically acceptable salt, solvate, or physiologically functional derivative thereof, and one or more therapeutic ingredients.

23. A combination according to claim 22 wherein the other therapeutic ingredient is selected from the group consisting of a PDE4 inhibitor, a corticosteroid, and an anticholinergic.

24. A combination comprising a compound according claim 4, or a physiologically acceptable salt, solvate, or physiologically functional derivative thereof, and one or more therapeutic ingredients.

25. A combination according to claim 24 wherein the other therapeutic ingredient is selected from the group consisting of a PDE4 inhibitor, a corticosteroid, and an anticholinergic.

* * * * *

UNITED STATES PATENT AND TRADEMARK OFFICE
CERTIFICATE OF CORRECTION

PATENT NO. : 7,045,658 B2
APPLICATION NO. : 10/472343
DATED : May 16, 2006
INVENTOR(S) : Keith Biggadike et al.

It is certified that error appears in the above-identified patent and that said Letters Patent is hereby corrected as shown below:

Title page 1, the title should read as follows:
  item (54) FORMANILIDE DERIVATIVES AS BETA2-ADRENORECEPTOR AGONISTS Title page, item (56) References Cited
  FOREIGN PATENT DOCUMENTS
  "GB    0416951    9/1991" should read --EP    0416951    3/1991

Column 20, line 51, "administration of" should read --administering--

Column 20, line 61, "pharmaceutically" should read --physiologically--

Column 21, line 1, Claim 9 should read as follows:

--A process for the preparation of a compound of formula (I), (Ia), or (Ib) according to any of claims 1 to 4, or a salt, solvate, or physiologically functional derivative thereof, which comprises:
  (a) deprotecting a protected intermediate of formula (II):

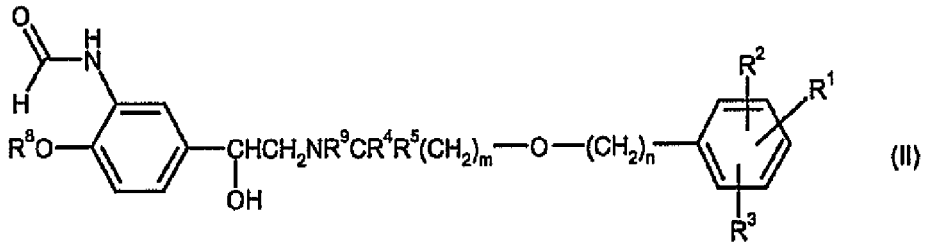

or a salt or solvate thereof, wherein $R^1$, $R^2$, $R^3$, $R^4$, $R^5$, m, and n are as defined for the compound of formula (I) in claim 1, and $R^8$, and $R^9$, are each independently either hydrogen or a protecting group provided that at least one of $R^8$, or $R^9$, is a protecting group optionally followed by one or more of the following steps in any order, wherein one or more steps is selected from the group consisting of:
  (i) removing any protecting groups;
  (ii) separating an enantiomer from a mixture of enantiomers; and
(iii) converting the product to a corresponding salt, solvate, or physiologically functional derivative thereof.--

UNITED STATES PATENT AND TRADEMARK OFFICE
CERTIFICATE OF CORRECTION

PATENT NO.         : 7,045,658 B2
APPLICATION NO. : 10/472343
DATED              : May 16, 2006
INVENTOR(S)       : Keith Biggadike et al.

It is certified that error appears in the above-identified patent and that said Letters Patent is hereby corrected as shown below:

The following claim should be added:

--26. A process for the preparation of a compound of formula (I), (Ia) or (Ib) according to any of claims 1 to 4, or a salt, solvate, or physiologically functional derivative thereof, which comprises:
    (a) reducing a compound of formula (III):

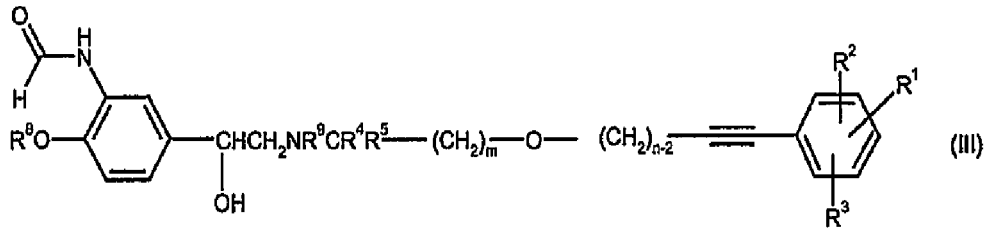

wherein $R^1$, $R^2$, $R^3$, $R^4$, $R^5$, m, and n are as defined for the compound of formula (I) in claim 1, and $R^8$, and $R^9$, are each independently either hydrogen or a protecting group; optionally followed by one or more of the following steps in any order, wherein one or more steps is selected from the group consisting of:
    (i) removing any protecting groups;
    (ii) separating an enantiomer from a mixture of enantiomers; and
    (iii) converting the product to a corresponding salt, solvate, or physiologically functional derivative thereof.--

Signed and Sealed this

Eighth Day of May, 2007

JON W. DUDAS
*Director of the United States Patent and Trademark Office*